(12) United States Patent
Kashikura et al.

(10) Patent No.: US 11,542,231 B2
(45) Date of Patent: Jan. 3, 2023

(54) METHOD OF PRODUCING FLUORINE-CONTAINING SULFIDE COMPOUNDS

(71) Applicant: KANTO DENKA KOGYO CO., LTD., Tokyo (JP)

(72) Inventors: Wataru Kashikura, Shibukawa (JP); Yoshihiko Iketani, Shibukawa (JP); Yuki Sato, Shibukawa (JP)

(73) Assignee: KANTO DENKA KOGYO CO., LTD., Tokyo (JP)

( * ) Notice: Subject to any disclaimer, the term of this patent is extended or adjusted under 35 U.S.C. 154(b) by 167 days.

(21) Appl. No.: 17/044,191

(22) PCT Filed: Mar. 29, 2019

(86) PCT No.: PCT/JP2019/013915
§ 371 (c)(1),
(2) Date: Sep. 30, 2020

(87) PCT Pub. No.: WO2019/189716
PCT Pub. Date: Oct. 3, 2019

(65) Prior Publication Data
US 2021/0047265 A1 Feb. 18, 2021

(30) Foreign Application Priority Data
Mar. 30, 2018 (JP) .............................. JP2018-069465

(51) Int. Cl.
*C07C 319/20* (2006.01)
*B01J 27/12* (2006.01)
(Continued)

(52) U.S. Cl.
CPC ............ *C07C 319/20* (2013.01); *B01J 27/12* (2013.01); *B01J 27/132* (2013.01); *B01J 21/18* (2013.01); *C07C 323/03* (2013.01)

(58) Field of Classification Search
CPC .......... B01J 27/12; B01J 27/132; B01J 21/18; C07C 17/093; C07C 319/20; C07C 323/03
See application file for complete search history.

(56) References Cited

U.S. PATENT DOCUMENTS 5,376,234 A 12/1994 Yanagida
6,127,587 A 10/2000 Williams
(Continued)

FOREIGN PATENT DOCUMENTS

DE 274820 A1 1/1990
JP H11049742 A 2/1999
(Continued)

OTHER PUBLICATIONS

Chenko, Tetraheterosubstituted methane with a carbon-halogen bond, (Science of synthesis (2005), 18, 1135-1201).*
(Continued)

*Primary Examiner* — Jafar F Parsa
(74) *Attorney, Agent, or Firm* — Browdy and Neimark, PLLC

(57) ABSTRACT

The present invention aims to provide a method by which fluorine-containing sulfide compounds, particularly sulfide compounds that contain hydrogen and fluorine, can be produced in a simple, low-cost and industrial manner. Provided is a method of producing a fluorine-containing sulfide compound represented by the following formula (2):

$$(F)_n\text{-}A^3\text{-}S\text{-}A^4\text{-}(F)_m \quad (2)$$

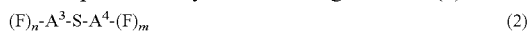

(wherein $A^3$ and $A^4$ are independently an optionally substituted hydrocarbyl group with a carbon number of 1 to 3; n and m represent the numbers of fluorine atoms binding to $A^3$ and $A^4$, with n+m=1 to 13 being satisfied), comprising reacting a chlorine-containing sulfide compound represented by the following formula (1):

$$(Cl)_n\text{-}A^1\text{-}S\text{-}A^2\text{-}(Cl)_m \quad (1)$$

(Continued)

(wherein $A^1$ and $A^2$ are independently an optionally substituted hydrocarbyl group with a carbon number of 1 to 3; n and m represent the numbers of chlorine atoms binding to $A^1$ and $A^2$, with n+m=1 to 13 being satisfied) and a fluorinating agent.

12 Claims, 1 Drawing Sheet

(51) Int. Cl.
    *B01J 27/132*      (2006.01)
    *B01J 21/18*      (2006.01)
    *C07C 323/03*      (2006.01)

(56) References Cited

U.S. PATENT DOCUMENTS

| | | |
|---|---|---|
| 6,316,636 B1 | 11/2001 | Rhone-Poulanc |
| 6,350,926 B1 * | 2/2002 | Williams ............... C07C 17/21 570/166 |
| 2009/0182179 A1 | 7/2009 | Merkel |

FOREIGN PATENT DOCUMENTS

| | | |
|---|---|---|
| JP | 3109253 B2 | 11/2000 |
| JP | 2001514645 A | 9/2001 |
| JP | 2009167187 A | 7/2009 |
| JP | 2012087092 A | 5/2012 |
| WO | 2016076183 A1 | 5/2016 |

OTHER PUBLICATIONS

S Gong et al.,"A Concise and Convenient Synthesis of 4-(Trifluoromethylthio)aniline" Asian Journal of Chemistry (2017),vol. 29, No. 1 ,pp. 91-93.

L.Saint-James, "Selective aliphatic fluorination by halogen exchange in mild conditions" Journal of Fluorine Chemistry(2006),(vol. 127),pp. 85-90.

R.E.A Dear et al., , "Preparation of Bis-[trifluoromethyl] Disulfide" Synthesis(1972),(vol. 6), p. 310.

Truce, William E., "Chlorination of dimethyly sulfide and some of its derivatives with sulfuryl chloride and thionyl chloride", Journal of the American Chemical Society, 1952, 74, pp. 3594-3599.

International Search Report for PCT/JP2019/013915.

* cited by examiner

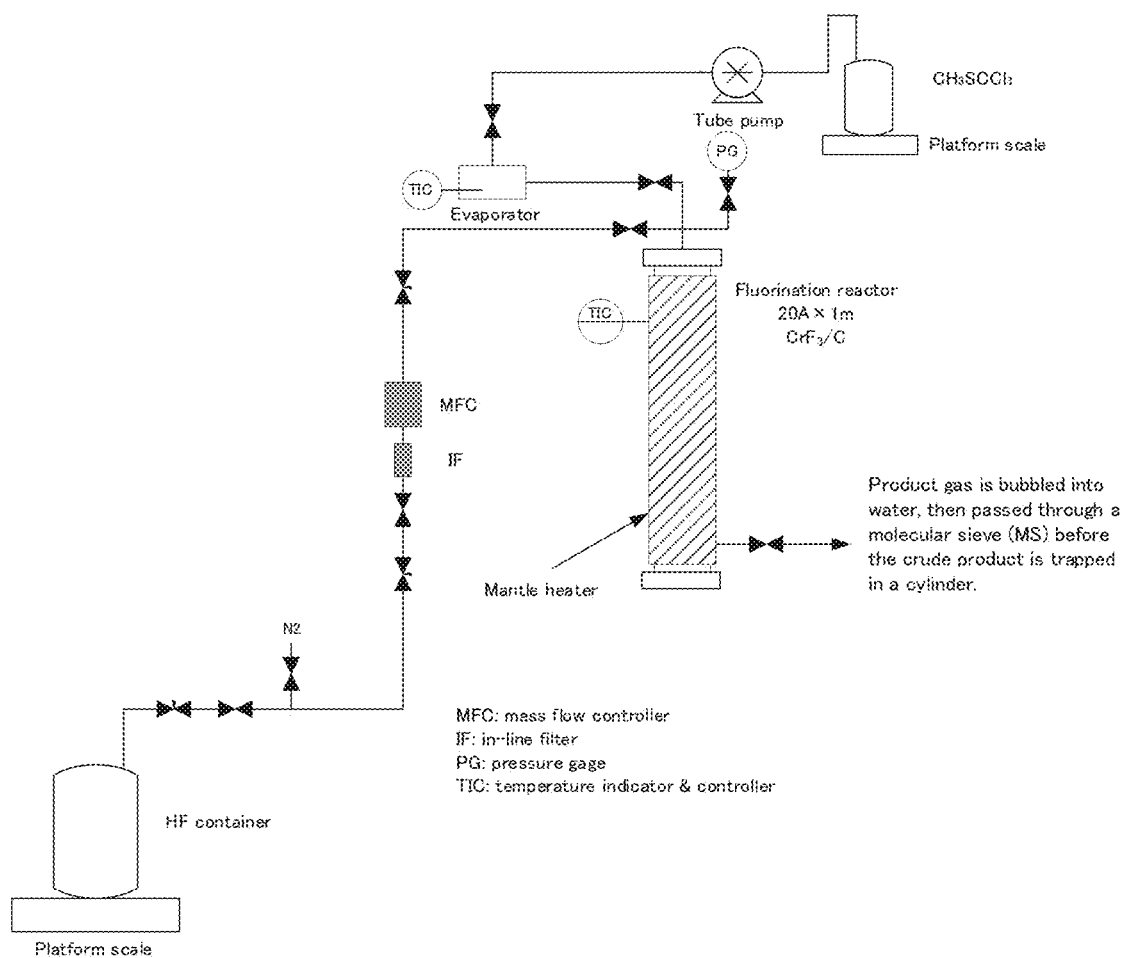

METHOD OF PRODUCING FLUORINE-CONTAINING SULFIDE COMPOUNDS

TECHNICAL FIELD

The present invention relates to a novel method of producing fluorine-containing sulfide compounds. The fluorine-containing sulfide compounds (also known as fluorine-containing thioethers) that are obtained by the method of the present invention are useful as gases intended for the application in specialty semiconductors and also as intermediates that can be derivatized to sulfone compounds to be utilized in agrochemicals, liquid electrolytes, etc.

BACKGROUND ART

As typically shown in Patent Document 1, fluorine-containing thioethers are useful as dry etching gases intended for the application in semiconductors. And a trifloromethylthio group of the type disclosed in Patent Document 2 is a useful substituent found in pharmaceutical and agrochemical compounds. And in Patent Document 3, fluorine-containing thioethers are also intermediates that can be derivatized to sulfone compounds that are used with advantage in liquid electrolytes.

Methods conventionally known to be capable of synthesizing these fluorine-containing thioethers include a reaction using thiophosgen as disclosed in Patent Document 2 and an addition reaction between thiols and olefins which is described in Patent Document 3; in recent years, reagents for introducing the trifloromethylthio group are the subject of active R&D efforts. Sulfur compounds such as thiophosgen and thiols have the problems of strong toxicity and extreme odor whereas the trifloromethylthio group introducing reagents are so expensive that they are difficult to produce on an industrial scale.

As far as the synthesis of aromatic sulfides is concerned, methods to synthesize fluorine-containing thioethers employing halogen exchange have been reported in many articles. Take, for example, Patent Document 4, in which 2-(trichloromethylthio)biphenyl is reacted with a fluorinating agent, allowing for the synthesis of 2-(trifluoromethylthio)biphenyl. According to Non-Patent Document 1, antimony trifluoride is used for converting a trichloromethylthio group to a trifluoromethylthio group in the step of synthesizing 4-(trifluoromethylthio)aniline.

To synthesize fluorine-containing thioethers from aliphatic sulfides by means of halogen exchange reaction, a trichloromethylthio group may be converted to a trifluoromethylthio group using a fluorinating agent of the type disclosed in Non-Patent Document 2 ((HF)$_{10}$-pyridine); however, this method requires at least 15 equivalents of the fluorinating agent and, what is more, in order to synthesize the fluorinating agent, a preparation need be made by mixing HF and an organic basic compound but then this causes problems such as an increased number of manufacturing steps and the organic basic compound becoming waste.

A method of converting a chained sulfur compound to a trifluoromethylthio group using a metal fluoride is described in Non-Patent Document 3, in which halogen exchange reaction is effected on bis-(trichloromethyl)disulfide using potassium fluoride. In the metal fluoride based halogen exchange reaction, at least a stoichiometric amount of the metal fluoride is required and after the reaction, a metal chloride and other by-products occur in the form of a slurry with the solvent used. What is more, the reactivity of the metal fluoride varies considerably with the particle size and shape used and its water content, so it is difficult to use the metal fluoride as a feed on an industrial scale.

CITATION LIST

Patent Documents

Patent Document 1: Japanese Patent No. 3109253
Patent Document 2: Re-publication of PCT International Publication WO2016/076183
Patent Document 3: JP 2012-87092 A1
Patent Document 4: JP H 11-49742 A1

Non-Patent Documents

Non-Patent Document 1: Asian Journal of Chemistry (2017), 29(1), 91-93.
Non-Patent Document 2: Journal of Fluorine Chemistry (2006), (127), 85-90.
Non-Patent Document 3: Synthesis (1972), (6), 310.

SUMMARY OF INVENTION

Technical Problem

It is an object of the present invention to provide a method by which fluorine-containing sulfide compounds, particularly sulfide compounds that contain hydrogen and fluorine, can be produced in a simple, low-cost and industrial manner.

Solution to Problem

The present invention provides the following.
[1] A method of producing a fluorine-containing sulfide compound represented by the following formula (2):

[Formula 2]

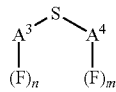

(2)

(wherein $A^3$ and $A^4$ are independently an optionally substituted hydrocarbyl group with a carbon number of 1 to 3; n and m represent the numbers of fluorine atoms binding to $A^3$ and $A^4$, with n+m=1 to 13 being satisfied), comprising reacting a chlorine-containing sulfide compound represented by the following formula (1):

[Formula 1]

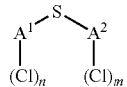

(1)

(wherein $A^1$ and $A^2$ are independently an optionally substituted hydrocarbyl group with a carbon number of 1 to 3; n and m represent the numbers of chlorine atoms binding to $A^1$ and $A^2$, with n+m=1 to 13 being satisfied) and a fluorinating agent.
[2] The method of producing a fluorine-containing sulfide compound as recited in [1], wherein the chlorine-containing sulfide compound represented by the formula (1) is represented by the following formula (3):

[Formula 3]

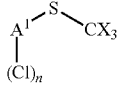

(3)

(wherein $A^1$ is an optionally substituted hydrocarbyl group with a carbon number of 1 to 3; X is a chlorine atom or a fluorine atom; n represents the number of chlorine atoms binding to $A^1$ and is in the range of 0 to 6, provided that when n is zero, at least one X is a chlorine atom), and wherein the fluorine-containing sulfide compound represented by the formula (2) is represented by the following formula (4):

[Formula 4]

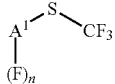

(4)

(wherein $A^1$ is an optionally substituted hydrocarbyl group with a carbon number of 1 to 3; n represents the number of fluorine atoms binding to $A^1$ and is in the range of 0 to 6).

[3] The method of producing a fluorine-containing sulfide compound as recited in [1] or [2], wherein the reaction is performed in the presence of a metal catalyst.

[4] The method of producing a fluorine-containing sulfide compound as recited in any one of [1] to [3], wherein the metal catalyst is supported on activated charcoal.

[5] The method of producing a fluorine-containing sulfide compound as recited in any one of [1] to [4], wherein the reaction is performed at a temperature of 50 to 350° C.

[6] The method of producing a fluorine-containing sulfide compound as recited in any one of [1] to [5], wherein the chlorine-containing sulfide compound and the fluorinating agent are vaporized before being supplied to a reactor.

Advantageous Effects of Invention

According to the present invention, fluorine-containing sulfide compounds, particularly sulfide compounds that contain hydrogen and fluorine, can be produced in a simple, low-cost and industrial manner. In particular, the method of the present invention can be implemented by mixing a chlorine-containing sulfide compound of formula (1) and a fluorinating agent, with the additional advantage of yielding a product that features high selectivity for a fluorine-containing sulfide compound of formula (2).

BRIEF DESCRIPTION OF DRAWINGS

FIG. 1 is a schematic diagram of an apparatus for producing fluorine-containing sulfide compounds that was used in the Examples.

DESCRIPTION OF EMBODIMENTS (Action)

The present invention relates to a method of producing a fluorine-containing sulfide compound represented by the above-described formula (2) which comprises reacting a chlorine-containing sulfide compound represented by the above-described formula (1) and a fluorinating agent. In the method of the present invention, the chlorine atoms in the compound of formula (1) are replaced by fluorine atoms by means of the fluorinating agent, whereupon the compound of formula (2) is selectively obtained. Before the accomplishment of the present invention, no report has been published on the case where the chlorine atoms in the chlorine-containing sulfide compound of the formula (1) were replaced by fluorine atoms by means of the fluorinating agent; what is more, the compound of formula (2) is obtained with high selectivity in the present invention, which is therefore a novel and useful invention.

(Starting feed)

In formula (1), $A^1$ and $A^2$ are independently an optionally substituted hydrocarbyl group with a carbon number of 1 to 3, and n and m specify the numbers of chlorine atoms binding to these hydrocarbyl groups. Since n+m=1 to 13 is satisfied, n and m are not both zero, and not all of the substituents on $A^1$ and $A^2$ are chlorine atoms.

The optionally substituted hydrocarbyl group with a carbon number of 1 to 3 may be exemplified by an optionally substituted alkyl group with a carbon number of 1 to 3, an optionally substituted alkenyl group with a carbon number of 2-3, an optionally substituted alkyl ether group with a carbon number of 1 to 3, and an optionally substituted alkyl ester group with a carbon number of 1 to 3. The optionally substituted alkyl group with a carbon number of 1 to 3 may be exemplified by a methyl group, an ethyl group, a propyl group, an isopropyl group, and groups derived from these alkyl groups by replacing part of the constituent hydrogen atoms with a substituent such as fluorine, chlorine, bromine, or iodine. The optionally substituted alkenyl group with a carbon number of 2-3 may be exemplified by a vinyl group, an allyl group, and groups derived from these alkenyl groups by replacing part of the constituent hydrogen atoms with a substituent such as fluorine, chlorine, bromine, or iodine. In formula (1), only the numbers of chlorine atoms are indicated but applicable substituents may be other than halogen atoms such as a hydroxyl group.

A more preferred example of the compound of formula (1) is a compound represented by formula (3). Symbol $A^1$ refers to an optionally substituted hydrocarbyl group with a carbon number of 1 to 3 and may be defined as explained with respect to formula (1). Symbol X refers to a chlorine or a fluorine atom, and n which represents the number of chlorine atoms binding to the hydrocarbyl group is in the range of 0 to 6. Since the compound of formula (3) also has at least one chlorine atom, at least one X need be a chlorine atom when n is zero.

Specific examples of the compound of formula (1) include, but are not limited to, the following:
$CH_3$—S—$CCl_3$, $CH_3$—S—$CHCl_2$, $CH_3$—S—$CH_2Cl$, $CH_2Cl$—S—$CH_2Cl$, $CH_2Cl$—S—$CHCl_2$, $CH_2Cl$—S—$CCl_3$, $CHCl_2$—S—$CCl_3$, $CHCl_2$—S—$CHCl_2$;
$CH_3CH_2$—S—$CCl_3$, $CH_3CH_2$—S—$CHCl_2$, $CH_3CH_2$—S—$CH_2Cl$;
n-Pr—S—$CCl_3$, n-Pr—S—$CHCl_2$, n-Pr—S—$CH_2Cl$;
i-Pr—S—$CCl_3$, i-Pr—S—$CHCl_2$, i-Pr—S—$CH_2Cl$;
$CH_3$—S—$CCl_2CCl_3$, $CH_3$—S—$CCl_2CHCl_2$, $CH_3$—S—$CCl_2CH_2Cl$;

$CH_3CH_2$—S—$CCl_2CCl_3$, $CH_3CH_2$—S—$CCl_2CHCl_2$, $CH_3CH_2$—S—$CCl_2CH_2Cl$;
n-Pr—S—$CCl_2CCl_3$, n-Pr—S—$CCl_2CHCl_2$, n-Pr—S—$CCl_2CH_2Cl$;
i-Pr—S—$CCl_2CCl_3$, i-Pr—S—$CCl_2CHCl_2$, i-Pr—S—$CCl_2CH_2Cl$; and $CH_2$=CH—S—$CCl_3$, wherein n-Pr means normal propyl group, and i-Pr means isopropyl group.
(Product)

As the reaction proceeds, the chlorine atoms in the starting feed are replaced by fluorine atoms, so the optionally substituted hydrocarbyl groups $A^3$ and $A^4$ with carbon numbers of 1 to 3 in, as well as n and m in formula (2) are as described with respect to $A^1$ and $A^2$. In the case where the starting feed is a compound represented by formula (3), the product obtained is a compound represented by formula (4). The optionally substituted hydrocarbyl group $A^1$ with a carbon number of 1 to 3, as well as X and n in formula (4) are as described with respect to formula (3). Specific examples of the product include those of the compound of formula (1) provided that all chlorine atoms involved are replaced by fluorine atoms.
(Reaction conditions)

The reaction of the present invention may be performed either non-catalytically or in the presence of a catalyst; however, in order to obtain a higher selectivity, the reaction is preferably performed in the presence of a catalyst. The catalyst may be exemplified by those which are used with the fluorinating agent in the art concerned and examples include: metal fluorides such as chromium fluoride, nickel fluoride, copper fluoride, silver fluoride, sodium fluoride, potassium fluoride, and cesium fluoride; metal chlorides such as chromium chloride and nickel chloride; metal catalysts such as chromium, copper, zinc, silver, magnesium, and titanium. The catalyst may be carried on a support and exemplary supports include activated charcoal, alumina, and zeolite. The amount of the catalyst (if it is carried on a support, the amount of the support is included) may be considerably small relative to the amount of the starting feed and usually, an amount on the order of 30-400 g is charged into a reactor in the case where the flow of the starting feed per unit time is 40-500 g/hr.

The reaction is desirably performed at a temperature of 50 to 350° C., particularly at a temperature of 100 to 250° C. If the temperature is too low, the reaction will not proceed and if it is too high, by-products will be generated in large amounts. Since the present invention can be performed in the temperature range of 50 to 350° C., the absence of the need for a special apparatus offers an additional advantage in the aspect of the running cost of the reaction apparatus.

The starting feed and the fluorinating agent can be supplied either in a liquid or gaseous state depending on the properties of these materials. Materials having boiling points of 100 to 250° C. at normal pressure are capable of vaporizing in the process of heating up to the reaction temperature, so these materials are advantageously reacted in a gaseous state. The quantitative ratio between the starting feed and the fluorinating agent is such that when the theoretical amount of the fluorinating agent required to convert all the chlorine in the starting feed to fluorine is assumed to be one equivalent, the amount of the fluorinating agent relative to the starting feed is set to be one equivalent or greater in terms of the substance's quantitative ratio, with the range of 1.0 to 20.0 equivalents being preferred, and the range of 2.0 to 4.0 equivalents being more preferred, in terms of the substance's quantitative ratio. Take, for example, the case where hydrogen fluoride (HF) is used as the fluorinating agent and reaction is carried out with both the starting feed and HF being in a gaseous state; since volume ratio can be regarded as equivalent ratio, the quantitative ratio between the starting feed and the fluorinating agent is preferably in the range of 1.0 to 20.0 equivalents, more preferably in the range of 2.0 to 4.0 equivalents, in terms of volume ratio if the theoretical amount of the fluorinating agent required to convert all the chlorine in the starting feed to fluorine is assumed to be one equivalent.

EXAMPLES

The present invention will be described by the following example which is by no means intended to limit the scope of the present invention.

Example 1

A reaction represented by the following reaction formula was performed.

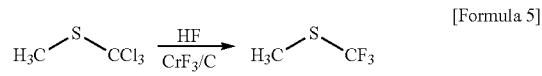

[Formula 5]

The reaction apparatus is shown in FIG. 1; predetermined amounts of a fluorinating agent (hydrogen fluoride: HF) and a starting feed (trichloromethylmethyl sulfide: $CH_3$—S—$CCl_3$) were introduced into a fluorination reactor packed with chromium trifluoride on activated charcoal ($CrF_3$/C) as obtained by the preparation method to be described later. Having a boiling point of 150° C. at normal pressure, the starting feed in liquid form was vaporized by heating at a heater temperature of 300° C. in an evaporator located upstream of the reactor. Having a boiling point of 20° C. at normal pressure hydrogen fluoride was vaporized by heating if necessary. The flow of the starting feed in a gaseous state and that of the fluorinating agent were allowed to converge at a point upstream of the reactor before they were supplied to the reactor. Heat was applied around the reactor by means of a mantle heater so that it was heated to a predetermined reaction temperature. The product gas exiting from the reactor was bubbled into water to remove the acid component, then passed through a molecular sieve (MS) column to thereby remove moisture, and recovered as a crude product. After analyzing the composition of the produced gas from the sampling sites at the exit of the reactor and downstream of the molecular sieve (MS) column, the crude gas was trapped.

Method of Preparing the Catalyst

Pure water <1000 g> and chromium (III) chloride hexahydrate <500 g> were intimately mixed at room temperature to obtain an aqueous solution of chromium chloride. The aqueous solution of chromium chloride and activated charcoal <900 g> were mixed so that the activated charcoal was impregnated with all of the chromium chloride over a period of 12 hours. Thereafter, the activated charcoal was dried at 60-80° C. for 2 days while introducing nitrogen. Thereafter, with $N_2$ being introduced, heating was effected by elevating the temperature up to 200° C. The dried chromium (III) chloride on activated charcoal <1.3 kg> was placed into the reactor shown in FIG. 1 and further dried at 300° C. while blowing nitrogen ($N_2$: 1-10 $m^3$). Under heating at 300° C., HF was introduced at 20-40 g/h (1-1.5 $m^3$ over a period of 10 hours). The spent catalyst may be regenerated for reuse.

Conditions for Analyzing the Produced Gas
Gas chromatographic analysis (GC analysis) <gas analysis>
  Column: Porapak-Q (3 φmm×3 m)
  Column temperature: 50-200° C. (5° C./min)
  Carrier gas: He
  Carrier gas flow: 50 mL/min
  Injection/detection temperature: 200° C.
  Detector: TCD GC purity was determined from the results of gas chromatographic analysis, with reference being made to the peak area for the end product (fluoride).

The results of Example 1 are shown in the following Table 1.

TABLE 1

| | Amount of $CH_3SCCl_3$ introduced | | Amount of HF introduced | | HF's equivalent amount[1] | Reaction temperature | Amount of catalyst packing (packaging height) | Space velocity[2] $h^{-1}$ in reactor | Linear velocity | Residence time | Crude yield |
|---|---|---|---|---|---|---|---|---|---|---|---|
| | g/h | mol/h | g/h | mol/h | eq. | ° C. | g(cm) | | m/s | s | (%) |
| Example 1 | 42.2 | 0.26 | 28 | 1.4 | 1.8 | 200 | 38 g(15 cm) | 98.1 | 0.027 | 36.7 | 70 |

| | Sampling location | $CO_2$ | $CHF_3$ | $CH_3F$ | $CF_3Cl$ | HCl | COS | HF + $CH_3Cl$ | $CH_3SCF_3$ | $CS_2$ | $CH_3SCFCl_2$ |
|---|---|---|---|---|---|---|---|---|---|---|---|
| | | | | | GC area % (exclusive of air) | | | | | | |
| Example 1 | Trap cylinder | 0.000 | 0.000 | 0.010 | 0.000 | 0.000 | 0.215 | 1.270 | 93.206 | 1.503 | 3.795 |

[1] Calculated as the equivalent amount required to convert the feed ($CH_3SCCl_3$) to $CH_3SCF_3$.
[2] Total flow (L/h)/reactor's volme (L)

From Table 1, the purity of the end compound (trifluoromethylmethyl sulfide: $CH_3$—S—$CF_3$) in the crud product as recovered in the trap cylinder was found to be 93% (in terms of GC).

From the result of Example 1, it was found that the selectivity of the end product ($CH_3$—S—$CF_3$) could be increased by setting the reaction temperature at around 200° C.

The invention claimed is:

1. A method of producing a fluorine-containing sulfide compound represented by the following formula (2):

[Formula 2]

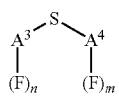

(2)

wherein $A^3$ and $A^4$ are independently a hydrocarbyl group with a carbon number of 1 to 3; n and m represent the numbers of fluorine atoms binding to $A^3$ and $A^4$, with n+m=1 to 13 being satisfied, comprising reacting a chlorine-containing sulfide compound represented by the following formula (1):

[Formula 1]

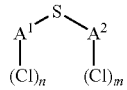

(1)

wherein $A^1$ and $A^2$ are independently a hydrocarbyl group with a carbon number of 1 to 3; n and m represent the numbers of chlorine atoms binding to $A^1$ and $A^2$, with n+m=1 to 13 being satisfied and a fluorinating agent, wherein the reaction is performed in the presence of at least one selected from the group consisting of metal fluorides supported on activated charcoal, metal chlorides supported on activated charcoal, and metal catalysts supported on activated charcoal.

2. A method of producing a fluorine-containing sulfide compound represented by the following formula (4):

[Formula 4]

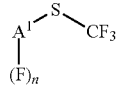

(4)

wherein $A^1$ is a hydrocarbyl group with a carbon number of 1 to 3; n represents the number of fluorine atoms binding to $A^1$ and is in the range of 0 to 6, comprising reacting a chlorine-containing sulfide compound represented by the following formula (3):

[Formula 3]

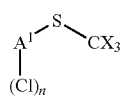

(3)

wherein $A^1$ is a hydrocarbyl group with a carbon number of 1 to 3; X is a chlorine atom or a fluorine atom; n represents the number of chlorine atoms binding to $A^1$ and is in the range of 0 to 6, provided that when n is zero, at least one X is a chlorine atom and a fluorinating agent, wherein the reaction is performed in the presence of at least one selected from the group consisting of metal fluorides supported on activated charcoal, metal chlorides supported on activated charcoal, and metal catalysts supported on activated charcoal.

3. The method of producing a fluorine-containing sulfide compound according to claim 1, wherein 1.0 to 20.0 equivalents of the fluorinating agent relative to the chlorine-containing sulfide compound is used in terms of the substance's quantitative ratio.

4. The method of producing a fluorine-containing sulfide compound according to claim 1, wherein the reaction is performed at a temperature of 50 to 350° C.

5. The method of producing a fluorine-containing sulfide compound according to claim 1, wherein the chlorine-containing sulfide compound and the fluorinating agent are vaporized before being supplied to a reactor.

6. The method of producing a fluorine-containing sulfide compound according to claim 1, wherein the at least one selected from the group consisting of metal fluorides supported on activated charcoal, metal chlorides supported on activated charcoal, and metal catalysts supported on activated charcoal is at least one selected from the group consisting of chromium fluoride, nickel fluoride, copper fluoride, silver fluoride, sodium fluoride, potassium fluoride, cesium fluoride, chromium chloride, nickel chloride, chromium, copper, zinc, silver, magnesium, and titanium, all of which is supported on activated charcoal.

7. The method of producing a fluorine-containing sulfide compound according to claim 1, wherein the chlorine-containing sulfide compound is $CH_3$—S—$CCl_3$, and the fluorine-containing sulfide compound is $CH_3$—S—$CF_3$.

8. The method of producing a fluorine-containing sulfide compound according to claim 7, wherein the fluorinating agent is hydrogen fluoride.

9. The method of producing a fluorine-containing sulfide compound according to claim 8, wherein the at least one selected from the group consisting of metal fluorides supported on activated charcoal, metal chlorides supported on activated charcoal, and metal catalysts supported on activated charcoal is $CrF_3$/C.

10. The method of producing a fluorine-containing sulfide compound according to claim 9, wherein 1.0 to 20.0 equivalents of the fluorinating agent relative to the chlorine-containing sulfide compound is used in terms of the substance's quantitative ratio.

11. The method of producing a fluorine-containing sulfide compound according to claim 10, wherein the reaction is performed at a temperature of 50 to 350° C.

12. The method of producing a fluorine-containing sulfide compound according to claim 11, wherein the chlorine-containing sulfide compound and the fluorinating agent are vaporized before being supplied to a reactor.

* * * * *